(12) United States Patent
Sakurai

(10) Patent No.: US 10,409,318 B2
(45) Date of Patent: Sep. 10, 2019

(54) INFORMATION PROCESSING DEVICE, INFORMATION PROCESSING METHOD, AND NON-TRANSITORY COMPUTER-READABLE RECORDING MEDIUM STORING INFORMATION PROCESSING PROGRAM

(71) Applicant: FUJITSU LIMITED, Kawasaki-shi, Kanagawa (JP)

(72) Inventor: Hiroshi Sakurai, Kawasaki (JP)

(73) Assignee: FUJITSU LIMITED, Kawasaki (JP)

( * ) Notice: Subject to any disclaimer, the term of this patent is extended or adjusted under 35 U.S.C. 154(b) by 278 days.

(21) Appl. No.: 15/655,942

(22) Filed: Jul. 21, 2017

(65) Prior Publication Data

US 2018/0046213 A1 Feb. 15, 2018

(30) Foreign Application Priority Data

Aug. 15, 2016 (JP) .................................. 2016-159362

(51) Int. Cl.

| | |
|---|---|
| *G06F 1/04* | (2006.01) |
| *G01N 30/62* | (2006.01) |
| *G06F 1/10* | (2006.01) |
| *G06F 1/08* | (2006.01) |
| *H03K 5/19* | (2006.01) |
| *H04L 1/20* | (2006.01) |
| *H04L 7/027* | (2006.01) |

(52) U.S. Cl.
CPC ............... *G06F 1/04* (2013.01); *G01N 30/62* (2013.01); *G01N 2030/626* (2013.01); *G06F 1/08* (2013.01); *G06F 1/10* (2013.01); *H03K 5/19* (2013.01); *H04L 1/205* (2013.01); *H04L 7/027* (2013.01)

(58) Field of Classification Search
CPC .... G01N 2030/626; G01N 30/62; G06F 1/04; G06F 1/08; G06F 1/10; H03K 5/19; H04L 1/205; H04L 7/02
See application file for complete search history.

(56) References Cited

U.S. PATENT DOCUMENTS

| | | | | |
|---|---|---|---|---|
| 5,528,198 A | * | 6/1996 | Baba ........................ | H04L 7/033 331/1 A |
| 2006/0097768 A1 | * | 5/2006 | Ijitsu ......................... | G06F 1/04 327/291 |
| 2011/0170644 A1 | * | 7/2011 | Iqbal ....................... | H04L 7/0337 375/355 |
| 2015/0155855 A1 | * | 6/2015 | Ma ......................... | H03K 3/017 327/175 |

FOREIGN PATENT DOCUMENTS

JP 2004-242243 8/2004

* cited by examiner

*Primary Examiner* — Terrell S Johnson
(74) *Attorney, Agent, or Firm* — Fujitsu Patent Center

(57) ABSTRACT

An information processing device includes: a receiver that compares a serial input signal to a threshold value and outputs reception data; an extraction circuit that extracts a clock superimposed on the reception data from the reception data; a measurement circuit that measures a pulse width of the reception data based on the clock; a counter that measures an elongation and a shortening of the pulse width; and an adjustment circuit that increases the threshold value when the elongation of the pulse width is larger than a reference value, and reduces the threshold value when the shortening of the pulse width is larger than the reference value.

15 Claims, 16 Drawing Sheets

INFORMATION PROCESSING DEVICE, INFORMATION PROCESSING METHOD, AND NON-TRANSITORY COMPUTER-READABLE RECORDING MEDIUM STORING INFORMATION PROCESSING PROGRAM

CROSS-REFERENCE TO RELATED APPLICATION

This application is based upon and claims the benefit of priority of the prior Japanese Patent Application No. 2016-159362, filed on Aug. 15, 2016, the entire contents of which are incorporated herein by reference.

FIELD

The embodiments discussed herein are related to an information processing device, an information processing method, and a recording medium storing an information processing program.

BACKGROUND

In an information processing device, high-speed serial transmission is performed.

The related art is discussed in Japanese Laid-open Patent Publication No. 2004-242243.

SUMMARY

According to an aspect of the embodiments, an information processing device includes: a receiver that compares a serial input signal to a threshold value and outputs reception data; an extraction circuit that extracts a clock superimposed on the reception data from the reception data; a measurement circuit that measures a pulse width of the reception data based on the clock; a counter that measures an elongation and a shortening of the pulse width; and an adjustment circuit that increases the threshold value when the elongation of the pulse width is larger than a reference value, and reduces the threshold value when the shortening of the pulse width is larger than the reference value.

The object and advantages of the invention will be realized and attained by means of the elements and combinations particularly pointed out in the claims.

It is to be understood that both the foregoing general description and the following detailed description are exemplary and explanatory and are not restrictive of the invention, as claimed.

DESCRIPTION OF EMBODIMENTS

Figure 1:
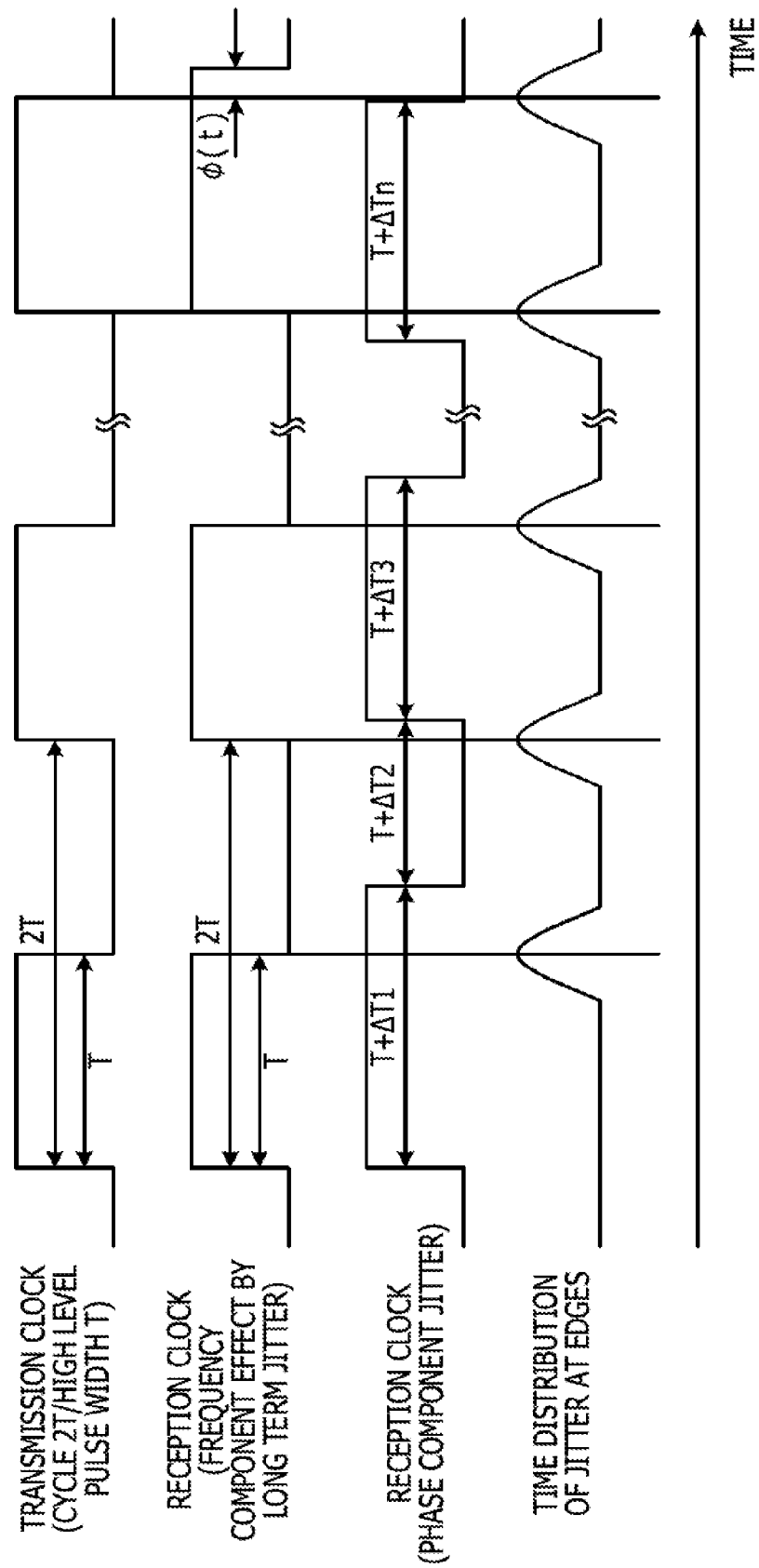
FIG. 1 is an example of jitter.

FIG. 1 is an example of a timing chart. A transmission clock having a cycle 2T transmitted from a transmission device is received by a reception device as a reception clock. For example, in the waveform of the reception clock, a frequency shift $\Phi(t)$ by long term jitter that affects a frequent component and a phase shift $\Delta Tn$ (here, "n" represents an integer) by phase jitter that affects a phase component occur. Such jitter prominently appears in high-speed serial transmission in which a clock is superimposed on data.

Figure 2:
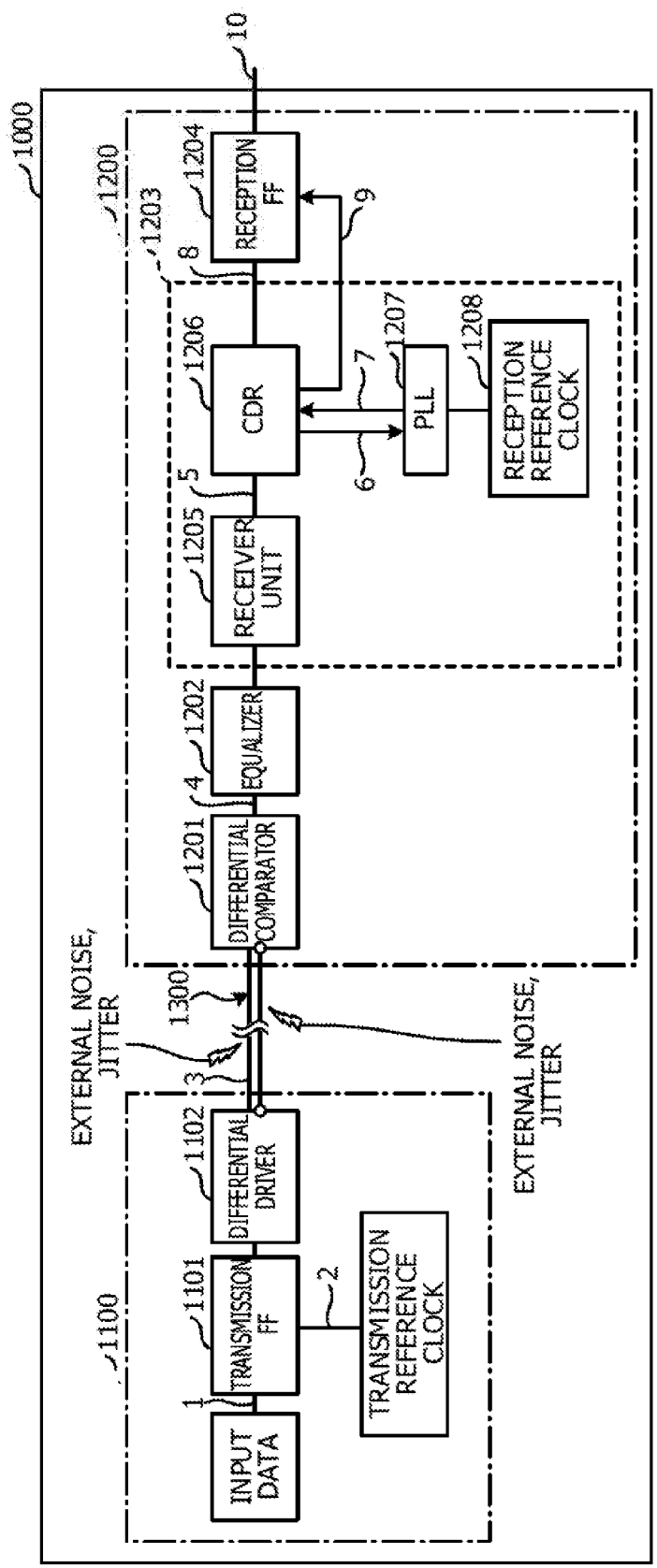
FIG. 2 is an example of an information processing device.
Figure 3:
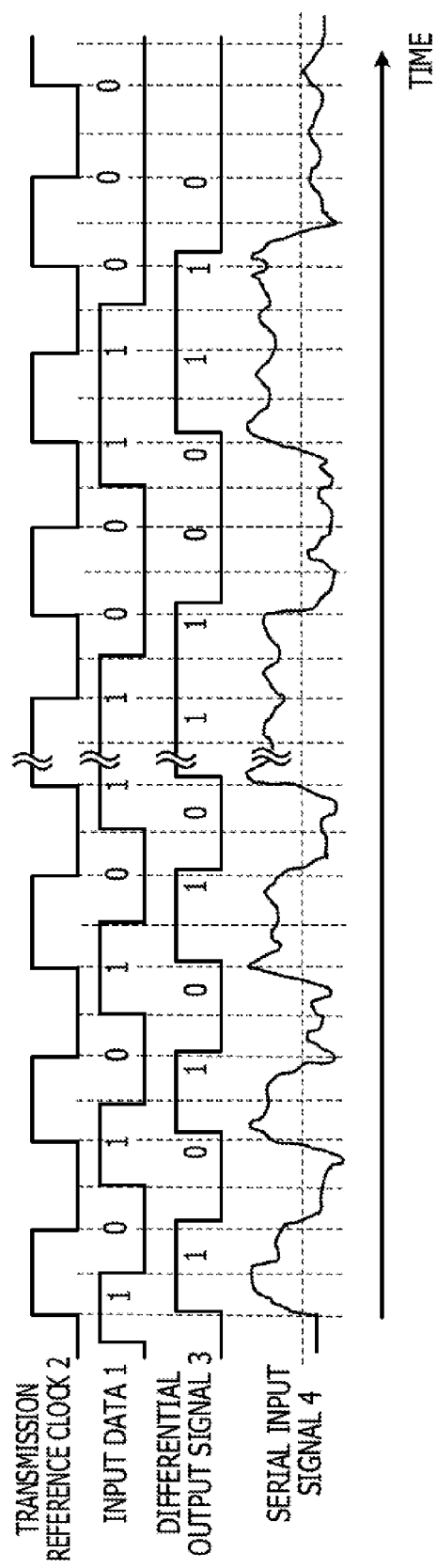
FIG. 3 is an example of signal processing.
Figure 4:
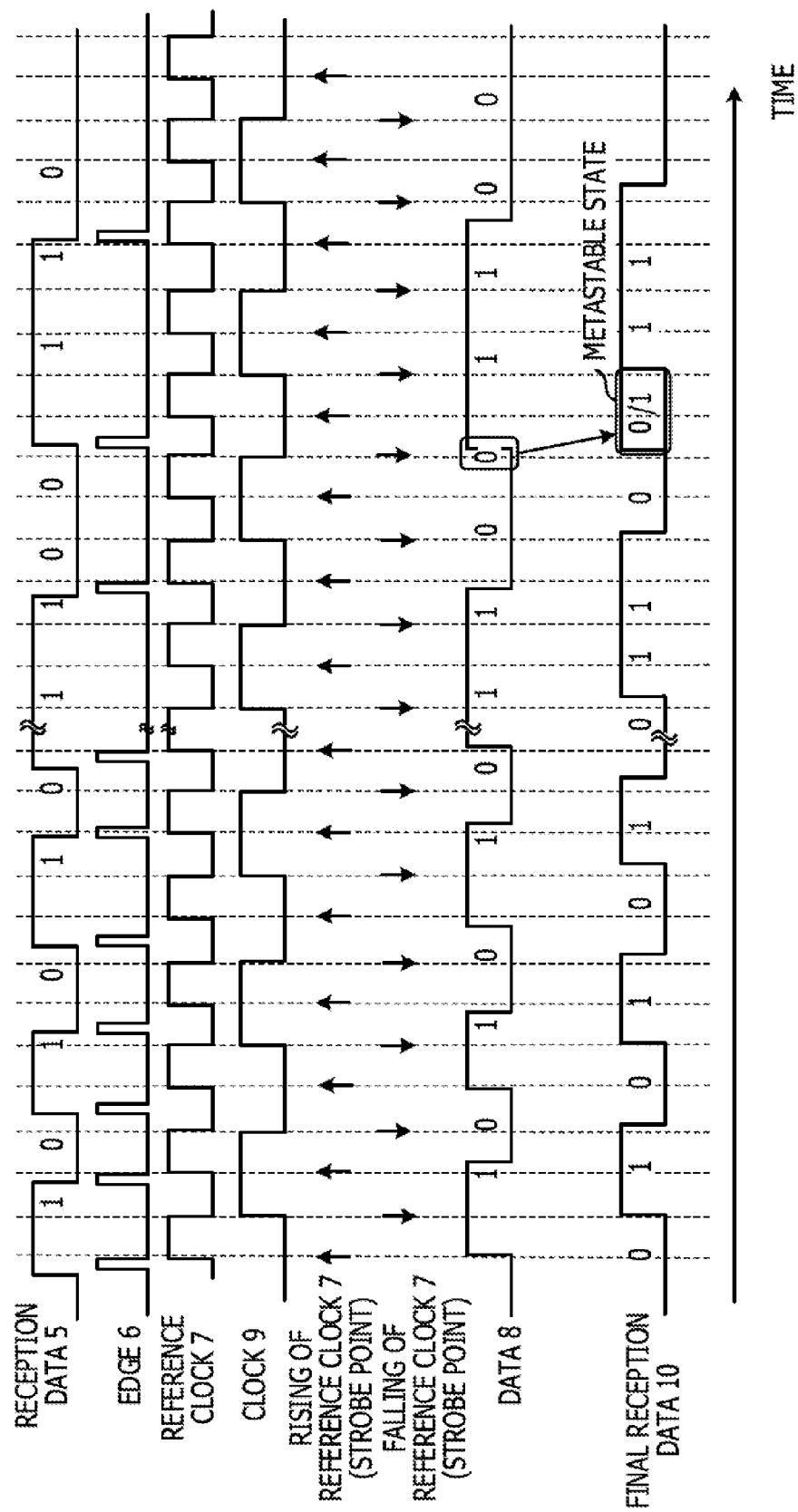
FIG. 4 is an example of the signal processing on the reception side.

FIG. 2 is an example of an information processing device. FIG. 2 illustrates a configuration of an information processing device 1000 using high-speed serial transmission in which a clock is superimposed on data. FIGS. 3 and 4 are examples each illustrating signal processing. FIG. 3 illustrates a timing chart indicating the signal processing on the transmission side of the information processing device. FIG. 4 illustrates a timing chart indicating the signal processing on the reception side of the information processing device.

The information processing device 1000 includes a transmission device 1100, a reception device 1200, and a transmission line 1300. The transmission device 1100 and the reception device 1200 are coupled to each other through the transmission line 1300. The transmission device 1100 includes a transmission FF 1101 and a differential driver 1102. The reception device 1200 includes a differential comparator 1201, an equalizer 1202, a reception processing unit 1203, and a reception FF 1204. The reception processing unit 1203 incudes a receiver unit 1205, a clock data recovery (CDR) 1206, and a phase locked loop (PLL) 1207.

An output of the transmission FF 1101 in which input data 1 is set in accordance with a transmission reference clock 2 is input to the differential driver 1102. The differential driver 1102 transmits a differential output signal 3 to the reception device 1200 through the transmission line 1300. After receiving the differential output signal 3, the differential comparator 1201 outputs a serial input signal 4. The serial input signal 4 shaped by the equalizer 1202 is input to the receiver unit 1205.

The receiver unit 1205 compares the serial input signal 4 input through the equalizer 1202 to a certain threshold value and outputs reception data 5. The CDR 1206 detects an edge 6 of the reception data 5, compares the phase of the edge 6 to the phase of an internal clock 7, and extracts clock 9 and data 8 from the reception data 5 on which the clock is superimposed. The internal clock 7 is a signal obtained by multiplying a reception reference clock 1208 by the PLL 1207. The reception FF 1204 generates final reception data 10 by latching the data 8 at the rising edge of the clock 9.

For example, jitter that occurs in the waveform of at least one of the clock 9 and the data 8 may not be fully corrected by the CDR 1206 and may become large. When the jitter becomes large, and at least one of a setup period and a hold period of the reception FF 1204 runs short, the final reception data 10 may become in the metastable state.

Figure 5:
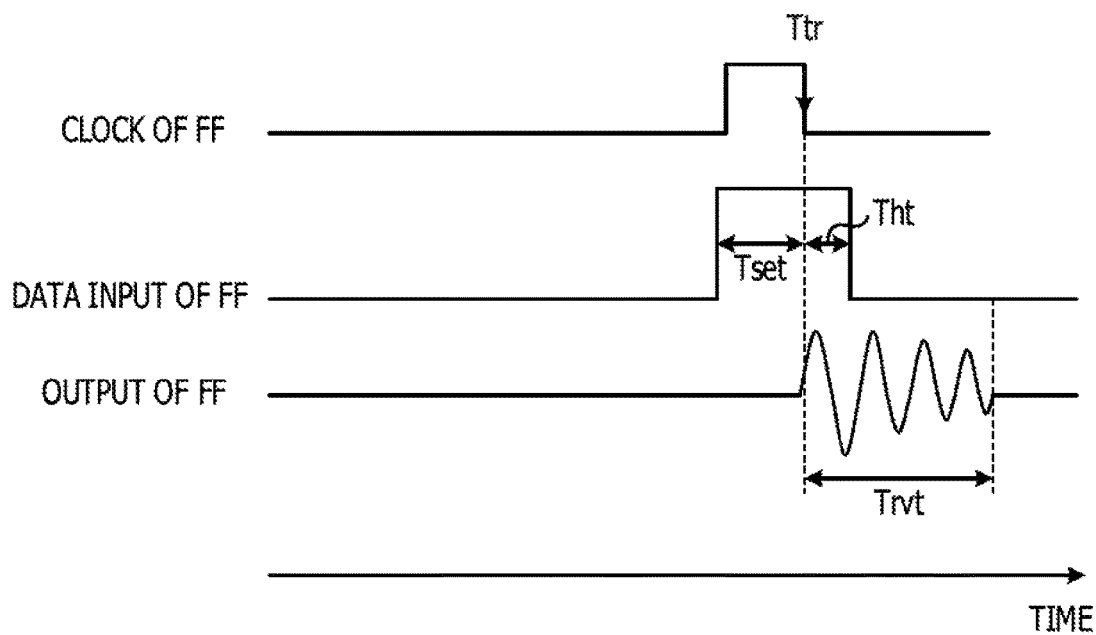
FIG. 5 is an example of a metastable state of a flip-flop (FF)

FIG. 5 is an example of the metastable state in an FF. The metastable state occurs when a setup period Tset or a hold period Tht of input data of the FF are not secured at the time of the clock input sampling edge Ttr of the FF. In the metastable state, the output of the FF becomes unstable in a recovery period Trvt. Therefore, when the next occurrence point of the clock input sampling edge Ttr is still in the recovery period Trvt, determination of the data may not be performed.

As described above, when the metastable state occurs due to the influence of the jitter, the determination of the data is not performed, so that an error rate of the serial transmission gets worse, and high-speed serial transmission may be inhibited.

For example, in the serial transmission in which a clock is superimposed on data, jitter may be reduced.

Figure 6:
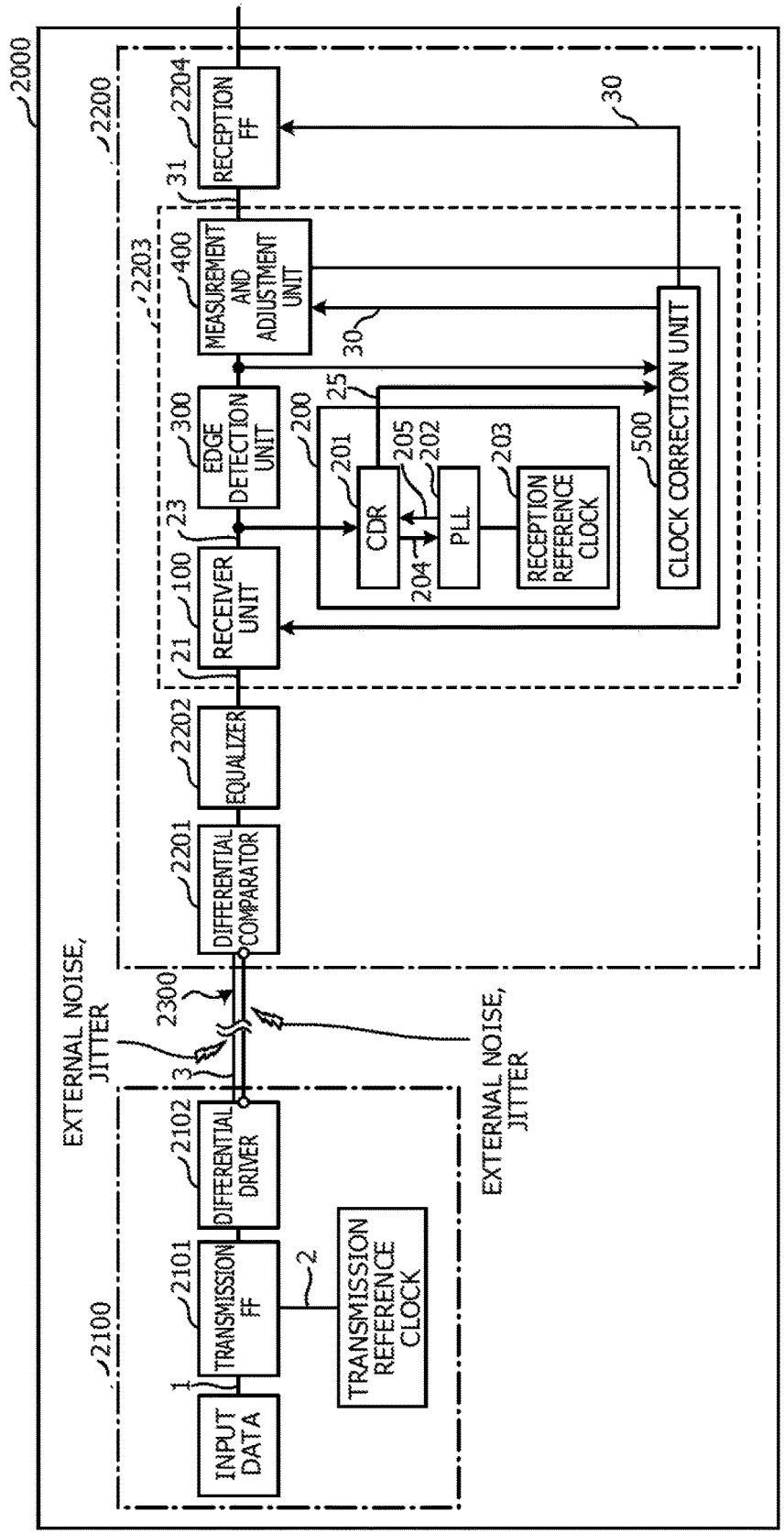
FIG. 6 is an example of an information processing device.

FIG. 6 is an example of an information processing device. FIG. 6 illustrates a configuration of an information processing device 2000 using high-speed serial transmission in which a clock is superimposed on data. The information processing device 2000 is an example of a device that processes information on data transmitted and received in the high-speed serial transmission in which a clock is superimposed on the data. As the information processing device 2000, a motherboard, a communication base station, a server, a mobile terminal device, a personal computer, or the like, may be applied. As the mobile terminal device, a mobile phone, a smartphone, or the like, may be applied. The information processing device 2000 is not limited to such examples.

The information processing device 2000 includes a transmission device 2100, a reception device 2200, and a transmission line 2300. The transmission device 2100 and the reception device 2200 are coupled to each other through the transmission line 2300. The transmission device 2100 includes a transmission FF 2101 and a differential driver 2102. The reception device 2200 includes a differential comparator 2201, an equalizer 2202, a reception processing unit 2203, and a reception FF 2204. The reception processing unit 2203 includes a receiver unit 100, a clock extraction unit 200, an edge detection unit 300, a measurement and an adjustment unit 400, and a clock correction unit 500.

An output of the transmission FF 2101 in which input data 1 is set in accordance with a transmission reference clock 2 is input to the differential driver 2102. The differential driver 2102 transmits a differential output signal 3 to the reception device 2200 through the transmission line 2300. After receiving the differential output signal 3, the differential comparator 2201 outputs a serial input signal 21. The serial input signal 21 shaped by the equalizer 2202 is input to the receiver unit 100 of the reception processing unit 2203.

The receiver unit 100 compares the serial input signal 21 input through the equalizer 2202 to an adjustable threshold value and outputs reception data 23. A CDR 201 of the clock extraction unit 200 detects an edge 204 of the reception data 23, compares the phase of the edge 204 to the phase of an internal clock 205, and extracts a clock 25 and data from the reception data 23 on which the clock is superimposed. The internal clock 205 is a signal obtained by multiplying a reception reference clock 203 by a PLL 202. The internal clock 205 and the clock 25 have the same frequency as the transmission reference clock 2.

For example, in the high-speed serial transmission in which a clock is superimposed on data, the data is set in accordance with the transmission reference clock 2, so that the data immediately after being output from the differential driver 2102, for example, before reaching the transmission line 2300 is almost perfectly synchronized with the multiplication number of the transmission reference clock 2. Therefore, immediately after the output from the differential driver 2102, the clock is superimposed on the data immediately after being output from the differential driver 2102 almost without shift. Every jitter such as random jitter due to irregular noise or the like input to the transmission line 2300 and periodically occurring deterministic jitter occurs at timing of signal transient along the transmission line 2300. Thus, the reception data received in the reception device 2200 and the clock extracted from the reception data are affected by the same type of jitter.

Therefore, the clock correction unit 500 generates a reference clock 30 obtained by correcting the clock 25 detected from the reception data 23 in the CDR 201 of the clock extraction unit 200 so that the metastable state does not occur in the reception FF 2204. In addition, the measurement and adjustment unit 400 generates correction data 31 obtained by correcting the reception data 23 so that the metastable state does not occur in the reception FF 2204.

For example, the clock correction unit 500 generates a plurality of reference clock pulses having different time differences with each other for the common clock 25 extracted from the reception data 23 in the CDR 201. The clock correction unit 500 selects a reference clock pulse to generate the correction data 31 that allows the reception FF 2204, to which the reference clock 30 is input, to securely have a setup period and a hold period, from among the generated plurality of reference clock pulses. The measurement and adjustment unit 400 generates the correction data 31 that is to be input to the reception FF 2204 using the selected reference clock pulse. The reception FF 2204 latches the correction data 31 in accordance with the reference clock 30.

The correction data 31 and the reference clock 30 are generated from the reception data 23 as described above, so that it is suppressed that the output of the reception FF 2204 may become in the metastable state, and sampling of the data may be performed accurately.

The edge detection unit 300 detects an edge of the reception data 23. The measurement and adjustment unit 400 measures a difference between the pulse width on the low level side of the reception data 23 and a value obtained by multiplying the pulse width of the transmission reference clock 2 having the duty ratio 50% by N, based on the detected edge, within a period defined in advance. Similarly, the measurement and adjustment unit 400 measures a difference between the pulse width on the high level side of the reception data 23 and the value obtained by multiplying the pulse width of the transmission reference clock 2 having the duty ratio 50% by N, based on the detected edge, within the period defined in advance. Here, "N" represents an integer. The differences measured by the measurement and adjustment unit 400 may be regarded as jitter amounts generated on the side of the transmission line 2300 and the reception device 2200, respectively.

For example, when the reception data 23 is fully synchronized with the transmission reference clock 2, the pulse width on the low level side and the pulse width on the high level side of the reception data 23 may correspond to N times the transmission reference clock 2. In order to compensate the jitter of the reception data 23, the measurement and adjustment unit 400 measures a difference between the pulse width on the low level side of the reception data 23 and a value obtained by multiplying the pulse width of the clock 25 having the duty ratio 50% by N, as an occurrence amount of the jitter, within the period defined in advance. Similarly, in order to compensate the jitter of the reception data 23, the measurement and adjustment unit 400 measures a difference between the pulse width on the high level side of the reception data 23 and the value obtained by multiplying the pulse width of the clock 25 having the duty ratio 50% by N, as an occurrence amount of the jitter, within the period defined in advance. The clock 25 may be replaced by the reference clock 30. The period defined in advance indicates a resynchronization period that is not corrected by a response period of the CDR 201, and for example, may correspond to a count number of 10K (here, "K" stands for 1000 times). For example, the measurement and adjustment unit 400 measures jitter amounts on the low level side and the high level side of the reception data.

The measurement and adjustment unit 400 adjusts a threshold value of the receiver unit 100 so that the measured difference approaches zero. For example, when there is no difference between jitter amounts on the low level side and the high level side, the measurement and adjustment unit 400 sets threshold value voltage of a comparator in the receiver unit 100, which is an example of a threshold value, at the center value of the threshold value voltage. The measurement and adjustment unit 400 sets the maximum count value of the difference on the high level side at the upper limit value possible as the threshold value voltage of the comparator in the receiver unit 100, and sets the maximum count value of the difference on the low level side at the lower limit value possible as the threshold value voltage of the comparator in the receiver unit 100. For example, the measurement and adjustment unit 400 sets voltage to a digital-to-analog (DA) converter and performs feedback of an analog output value of the DA converter to the receiver unit 100 to adjust the threshold value voltage of the comparator in the receiver unit 100.

The measurement and adjustment unit 400 measures the pulse width of the reception data 23 based on the clock 25 and measures an elongation and a shortening of the measured pulse width. The measurement and adjustment unit 400 increases the threshold value voltage of the comparator in the receiver unit 100 when the measured elongation is larger than a certain reference value and decreases the threshold value voltage when the measured shortening is larger than the certain reference value. When the threshold value voltage increases, the pulse width on the high level side of the reception data 23 is shortened, and the pulse width on the low level side of the reception data 23 is elongated. When the threshold value voltage is reduced, the pulse width on the low level side of the reception data 23 is shortened, and the pulse width on the high level side of the reception data 23 is elongated.

The threshold value voltage of the comparator in the receiver unit 100 is adjusted as described above, so that the jitter of the reception data 23 may be reduced. As a result, the influence of the jitter is reduced, so that the transmission rate is increased, and the transmission line length is extended, or the number of connectors inserted into the transmission line (the number of connectors through which the data passes) may be reduced.

For example, the measurement and adjustment unit 400 may increase the threshold value voltage when the elongation of the pulse width on the high level side of the reception data 23 is larger than the certain reference value, and reduce the threshold value voltage when the elongation of the pulse width on the low level side of the reception data 23 is larger than the certain reference value. Even when the threshold value voltage is adjusted as described above, the jitter of the reception data 23 may be reduced.

For example, a jitter amount is normally distributed. The frequency of the internal clock 205 may be set at the same value as the value of the frequency of the transmission reference clock 2 on the transmission side. Thus, the measurement and adjustment unit 400 on the reception side measures the pulse width of the reception data 23 statistically. The measurement and adjustment unit 400 dynamically corrects the pulse width of the reception data 23 by changing the threshold value of the receiver unit 100 based on the measurement result, for example, an average value of the measurement values of the pulse width, or the like. Therefore, the jitter may be corrected.

For example, in FIG. 1, the cycle of the reception clock is represented by "2T+$\Delta$Tn−1+$\Delta$Tn". For an expected value of the cycle of the transmission clock, "$\Delta$Tn−1+$\Delta$Tn=0" and "|$\Delta$Tn−1|=|$\Delta$Tn|" are satisfied. Thus, for example, when the reception processing unit 2203 corrects the reception data 23 so that "2T=2T+$\Delta$Tn−1+$\Delta$Tn", "$\Delta$T1n−1+$\Delta$Tn=0", "|$\Delta$Tn−1|=|$\Delta$Tn|", and "$\varphi$(t)=0" are satisfied, the influence of the jitter may be reduced.

The measurement and adjustment unit 400 corrects the pulse width of the reception data 23 by measuring the pulse width of the reception data 23 and performing feedback of a variation per a unit of time of the measured pulse width to the receiver unit 100 that is at a previous stage. Therefore, the jitter may be reduced, and the frequency shift $\Phi(t)$ and the phase shift $\Delta$Tn may be minimized. Due to the reduction in the jitter, the transmission line length may be increased, and the limitation of the number of connectors inserted along the transmission line may be reduced.

When the reception FF 2204 illustrated in FIG. 6 latches the correction data 31 output from the measurement and adjustment unit 400 in accordance with the reference clock 30 generated in the clock correction unit 500, reliable sampling of the reception data 23 may be performed. The jitter due to extension of wiring and an increase in the number of connectors is reduced, so that the bit error rate may be improved, or the transmission rate may be increased.

In reception of a high-speed serial signal in which a clock is superimposed on data, occurrence of the metastable state between the data and the clock detected in the CDR due to the influence of the jitter may be reduced even without a re-timer device. The re-timer device is an example of a device that receives data, on which sampling is performed with an internal clock, and superimposes a clock on the data again. When the variation in the time axis of the pulse width of the reception data 23 is fed back to the receiver unit 100 that is at the previous stage, the unstable operation of the reception FF 2204 that is at the latter stage may be reduced.

Even when a re-timer device is used, the transmission line length from the transmission side to the re-timer device is extended, and the limitation of the number of connectors each of which affects the jitter along the transmission line may be reduced. When a plurality of re-timer devices is used, the number of re-timer devices may be reduced.

Figure 7:
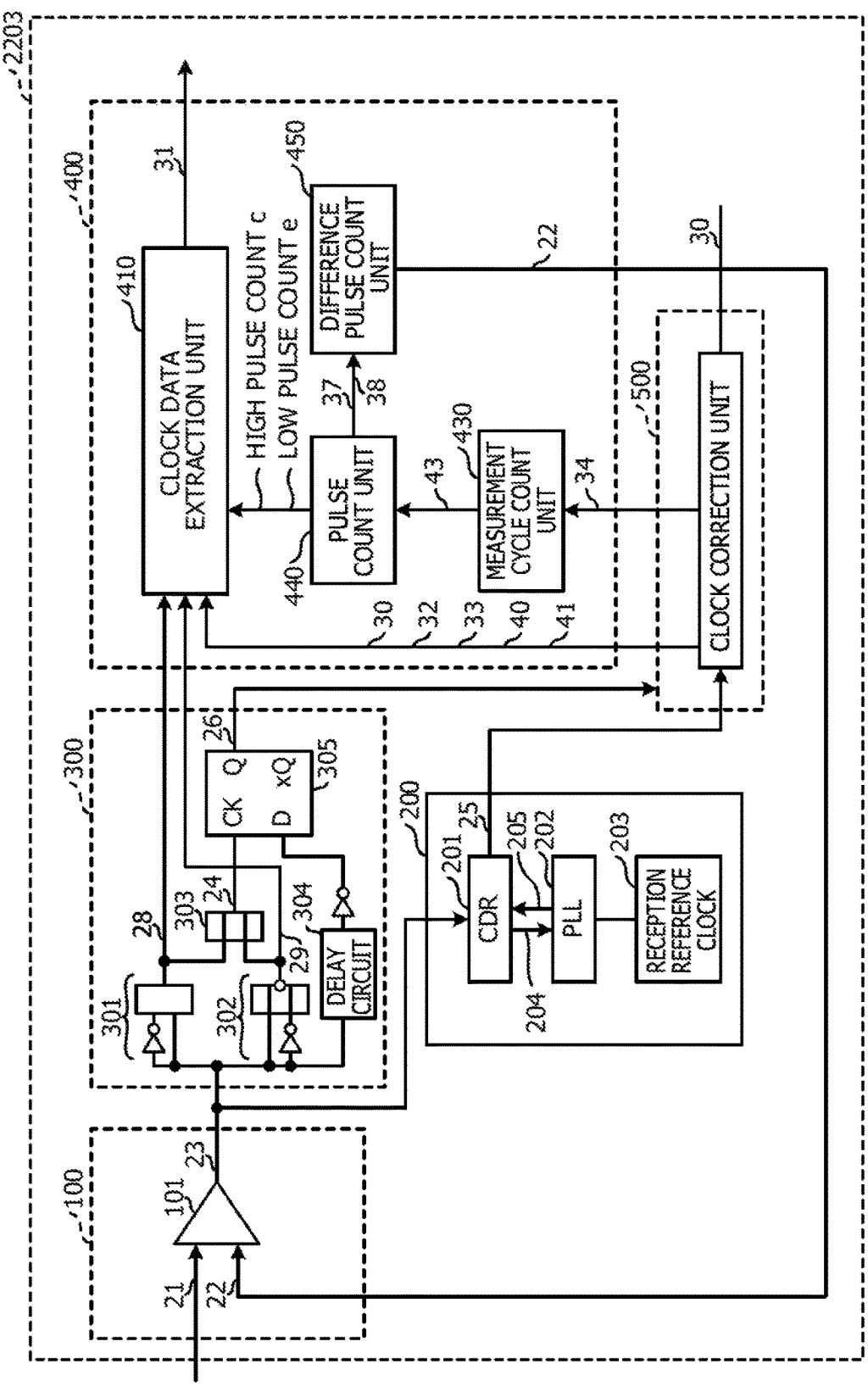
FIG. 7 is an example of a reception processing unit.

FIG. 7 is an example of the reception processing unit. The reception processing unit 2203 includes the receiver unit 100, the clock extraction unit 200, the edge detection unit 300, the measurement and adjustment unit 400, and the clock correction unit 500.

The receiver unit 100 receives the serial input signal 21 input through the equalizer 2202. The receiver unit 100 includes a comparator circuit 101. The comparator circuit 101 compares the serial input signal 21 to threshold value voltage 22, and outputs reception data 23 indicating the comparison result of the sizes of the serial input signal 21 and the threshold value voltage 22. When the voltage of the serial input signal 21 is higher than the threshold value voltage 22, for example, the comparator circuit 101 outputs reception data 23 having a high level "1". In addition, when the voltage of the serial input signal 21 is lower than the threshold value voltage 22, for example, the comparator circuit 101 outputs reception data 23 having a low level "0".

The threshold value voltage 22 is an example of a threshold value compared to the serial input signal 21. The threshold value voltage 22 is threshold value voltage used to determine whether the level of the serial input signal 21 is a high level or a low level. The threshold value voltage 22 is determined by a difference pulse count unit 450 in the measurement and adjustment unit 400.

The upper limit value and the lower limit value of the threshold value voltage 22 may be determined depending on a used input/output serial interface. As the input/output serial interface, peripheral component interconnect (PCI) express (PCIe), a statistical analysis system (SAS), or the like, may be used. When the serial input signal 21 is a differential signal, the upper limit value of the threshold value voltage 22 is set at the maximum value of receiver path sensitivity voltage, and the lower limit value of the threshold value voltage 22 is set at the minimum value of the receiver path sensitivity voltage. The threshold value voltage 22 is caused to become variable within the range of the upper limit value and the lower limit value by the difference pulse count unit 450.

The edge detection unit 300 extracts a rising edge 28 and a falling edge 29 of the pulse of the reception data 23. The rising edge 28 and the falling edge 29 are used to generate correction data 31 in the measurement and adjustment unit 400.

The edge detection unit 300 includes a rising edge detection circuit 301, a falling edge detection circuit 302, an OR circuit 303, a delay circuit 304, and a D-type FF (DFF) 305. The rising edge detection circuit 301 detects the rising edge 28 of the pulse of the reception data 23. The falling edge detection circuit 302 detects the falling edge 29 of the pulse of the reception data 23. The OR circuit 303 generates an edge output 24 that is an OR between the output of the rising edge detection circuit 301 and the output of the falling edge detection circuit 302. The delay circuit 304 causes the reception data 23 to be delayed by a certain period. The DFF 305 includes a clock input terminal CK to which the edge output 24 is input, a data input terminal D to which an output of the delay circuit 304 is input, and a data output terminal Q through which a DFF output status 26 is output. The DFF output status 26 indicates data held by the DFF 305.

The clock extraction unit 200 includes the CDR 201 and the PLL 202. The CDR 201 detects an edge 204 of the reception data 23, compares the phase of the edge 204 to the phase of the internal clock 205, and extracts a clock 25 superimposed on the reception data 23. The internal clock 205 may be a signal obtained by multiplying the reception reference clock 203 by the PLL 202. The internal clock 205 and the clock 25 may have the same frequency as the transmission reference clock 2.

The clock correction unit 500 generates a plurality of reference clock pulses by which the metastable state is not caused to occur in the FF of the measurement and adjustment unit 400 and a reference clock 30 used in the measurement and adjustment unit 400 and the reception FF 2204. The clock correction unit 500 corrects the clock 25, generates the reference clock 30 that is the corrected clock 25, and supplies the reference clock 30 to the measurement and adjustment unit 400 and the reception FF 2204.

Figure 8:
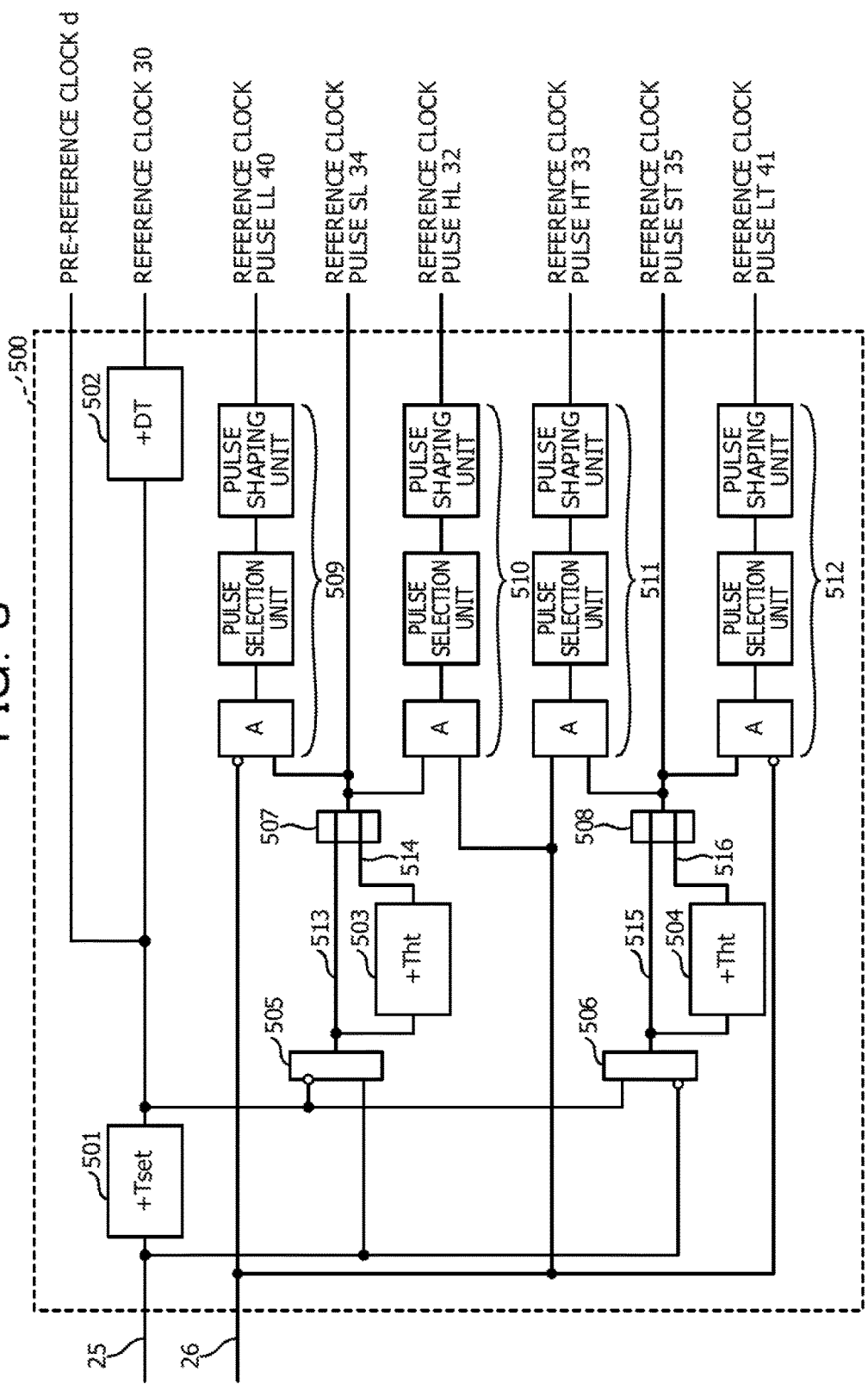
FIG. 8 is an example of a clock correction unit.

FIG. 8 is an example of the clock correction unit. The clock correction unit 500 includes delay circuits 501 to 504, AND circuits 505 and 506, OR circuits 507 and 508, and short pulse removal circuits 509 to 512. Each of the short pulse removal circuits 509 to 512 includes an AND circuit A, a pulse selection unit, and a pulse shaping unit. Here, "○" in each of the input units of the AND circuits 505 and 506 and the AND circuit A indicates a logic NOT circuit. A similar condition is applied to "○" illustrated in the other diagrams.

When the clock 25 is set as a clock for the reception FF 2204, the delay circuit 501 generates a pre-reference clock d obtained by delaying the clock 25 by the setup period Tset desired for the reception FF 2204.

The delay circuit 502 generates a reference clock 30 obtained by delaying the pre-reference clock d by the delay period DT that occurs in each of the short pulse removal circuits 509 to 512. The short pulse removal circuits 509 to 512 have an equal delay period DT. The delay period DT is a sum of the delay period A of at least one of the logic circuits, the setup period of at least one of the FFs, and the hold period of at least one of the FFs.

The clock correction unit 500 generates a reference clock pulse SL 34 so that the DFF output status 26 is not caused to become the metastable state by the reference clock 30. The delay circuit 503 generates a clock 514 obtained by delaying the clock 513 by the hold period Tht desired for the reception FF 2204 when the reception FF 2204 is set at the rising edge of the reference clock 30. The clock 513 is output from the AND circuit 505. The OR circuit 507 generates the reference clock pulse SL 34 by which the DFF output status 26 is not caused to become the metastable state at the rising edge of the reference clock 30 by calculating an OR between the clock 513 and the clock 514.

In order to generate an input signal by which the DFF output status 26 that is input data is not caused to become the metastable state, a short pulse removal circuit 510 calculates an AND between the reference clock pulse SL 34 and the DFF output status 26 in the AND circuit A. The short pulse removal circuit 510 generates a reference clock pulse HL 32 obtained by removing merely a pulse that causes the metastable state to occur in the DFF output status 26 from a signal of the AND between the reference clock pulse SL 34 and the DFF output status 26 by selecting and shaping the signal. Therefore, sampling by the rising edge of the reference clock 30 at timing of the pulse removed from the signal of the AND between the reference clock pulse SL 34 and the DFF output status 26 is reduced. The reference clock pulse HL 32 is generated that is set so that the pulse on the high level side of the DFF output status 26 is not caused to become the metastable state by the rising edge of the reference clock 30.

Similarly, in order to generate an input signal by which the DFF output status 26 that is the input data is not caused to become the metastable state, the short pulse removal circuit 509 calculates an AND between the reference clock pulse SL 34 and the negative logic of the DFF output status 26 in the AND circuit A. The short pulse removal circuit 509 generates a reference clock pulse LL 40 obtained by removing merely a pulse that causes the metastable state to occur in the DFF output status 26 from a signal of the AND between the reference clock pulse SL 34 and the negative logic of the DFF output status 26 by selecting and shaping the signal. Therefore, sampling by the rising edge of the reference clock 30 at timing of the pulse removed from the signal of the AND between the reference clock pulse SL 34 and the negative logic of the DFF output status 26 is reduced. The reference clock pulse LL 40 is generated that is set so that the pulse on the low level side of the DFF output status 26 is not caused to become the metastable state by the rising edge of the reference clock 30.

The clock correction unit 500 generates a reference clock pulse ST 35 so that the DFF output status 26 is not caused to become the metastable state by the reference clock 30. The delay circuit 504 generates a clock 516 obtained by delaying a clock 515 by the hold period Tht desired for the reception FF 2204 when the reception FF 2204 is set at the falling edge of the reference clock 30. The clock 515 is output from the AND circuit 506. The OR circuit 508 generates a reference clock pulse ST 35 by which the DFF output status 26 is not caused to become the metastable state at the falling edge of the reference clock 30 by calculating an OR between the clock 515 and the clock 516.

Figure 9:
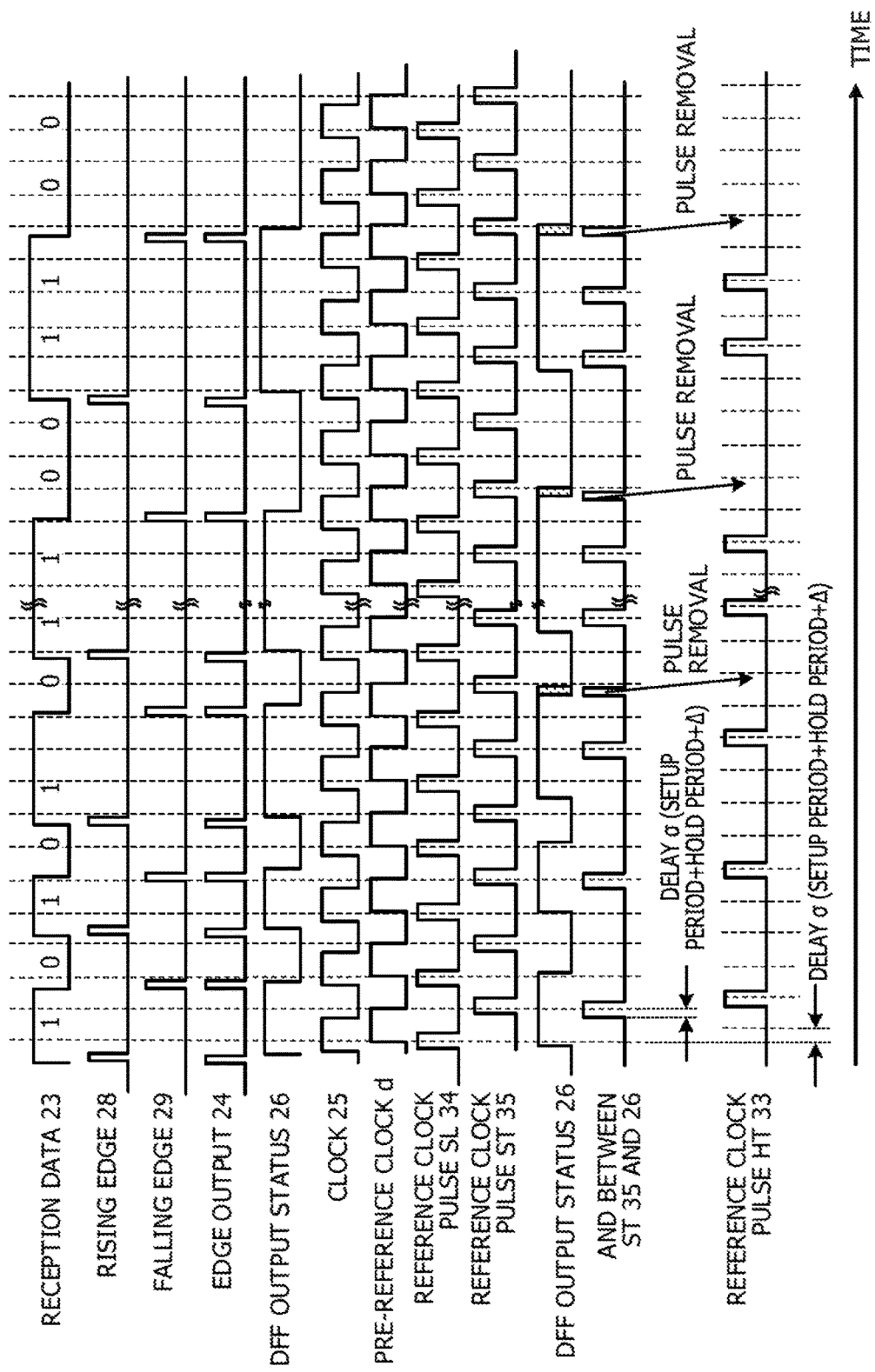
FIG. 9 is an example of processing in an edge detection unit and a clock correction unit.

In order to generate an input signal by which the DFF output status 26 that is the input data is not caused to become the metastable state, a short pulse removal circuit 511 calculates an AND between the reference clock pulse ST 35 and the DFF output status 26 in the AND circuit A. The short pulse removal circuit 511 generates a reference clock pulse HT 33 obtained by removing merely a pulse that causes the metastable state to occur in the DFF output status 26 from a signal of the AND between the reference clock pulse ST 35 and the DFF output status 26 by selecting and shaping the signal. Therefore, sampling by the falling edge of the reference clock 30 at timing of the pulse removed from the signal of the AND between the reference clock pulse ST 35 and the DFF output status 26 is reduced. The reference clock pulse HT 33 is generated that is set so that the pulse on the high level side of the DFF output status 26 is not caused to become the metastable state by the falling edge of the reference clock 30. FIG. 9 is an example of processing in the edge detection unit and the clock correction unit. In FIG. 9, for example, the reference clock pulse HT 33 is generated.

Similarly, in order to generate an input signal by which the DFF output status 26 that is the input data is not caused to become the metastable state, a short pulse removal circuit 512 calculates an AND between the reference clock pulse ST 35 and the negative logic of the DFF output status 26 in the AND circuit A. The short pulse removal circuit 512 generates a reference clock pulse LT 41 obtained by removing merely a pulse that causes the metastable state to occur in the DFF output status 26 from a signal of the AND between the reference clock pulse ST 35 and the negative logic of the DFF output status 26 by selecting and shaping the signal. Therefore, sampling by the falling edge of the reference clock 30 at timing of the pulse removed from the signal of the AND between the reference clock pulse ST 35 and the negative logic of the DFF output status 26 is reduced. The reference clock pulse LT 41 is generated that is set so that the pulse on the low level side of the DFF output status 26 is not caused to become the metastable state by the falling edge of the reference clock 30.

Figure 10:
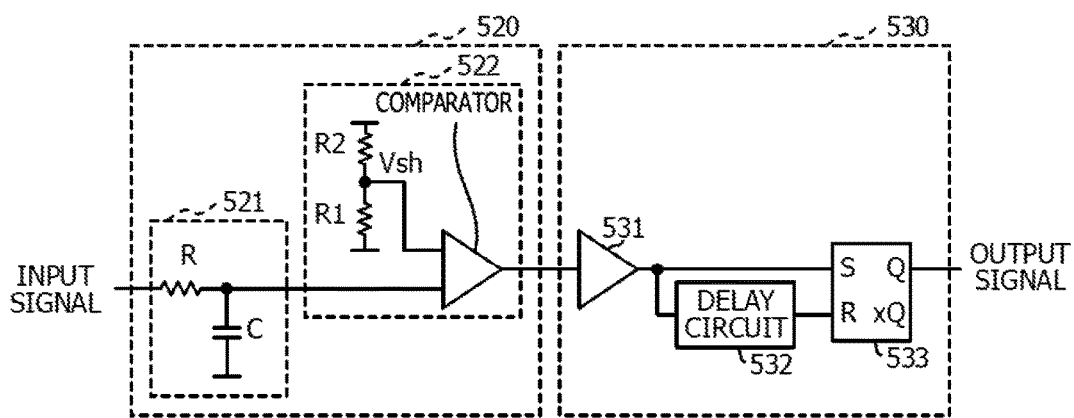
FIG. 10 is an example of a short pulse removal circuit.

FIG. 10 is an example of the short pulse removal circuit. Each of the short pulse removal circuits 509 to 512 includes a pulse selection unit 520 and a pulse shaping unit 530. The pulse selection unit 520 includes an integration circuit 521 and a slice level comparison circuit 522. The integration circuit 521 includes an RC circuit constituted by a resistor R and a capacitor C. The slice level comparison circuit 522 includes a comparator that compares a slice level Vsh generated by a resistor R1 and a resistor R2 to a signal output from the integration circuit 521. The pulse shaping unit 530 includes a schmidt trigger 531, a delay circuit 532, and an RS-type FF (RSFF) 533. An output of the comparator is input to the schmidt trigger 531.

Figure 11:
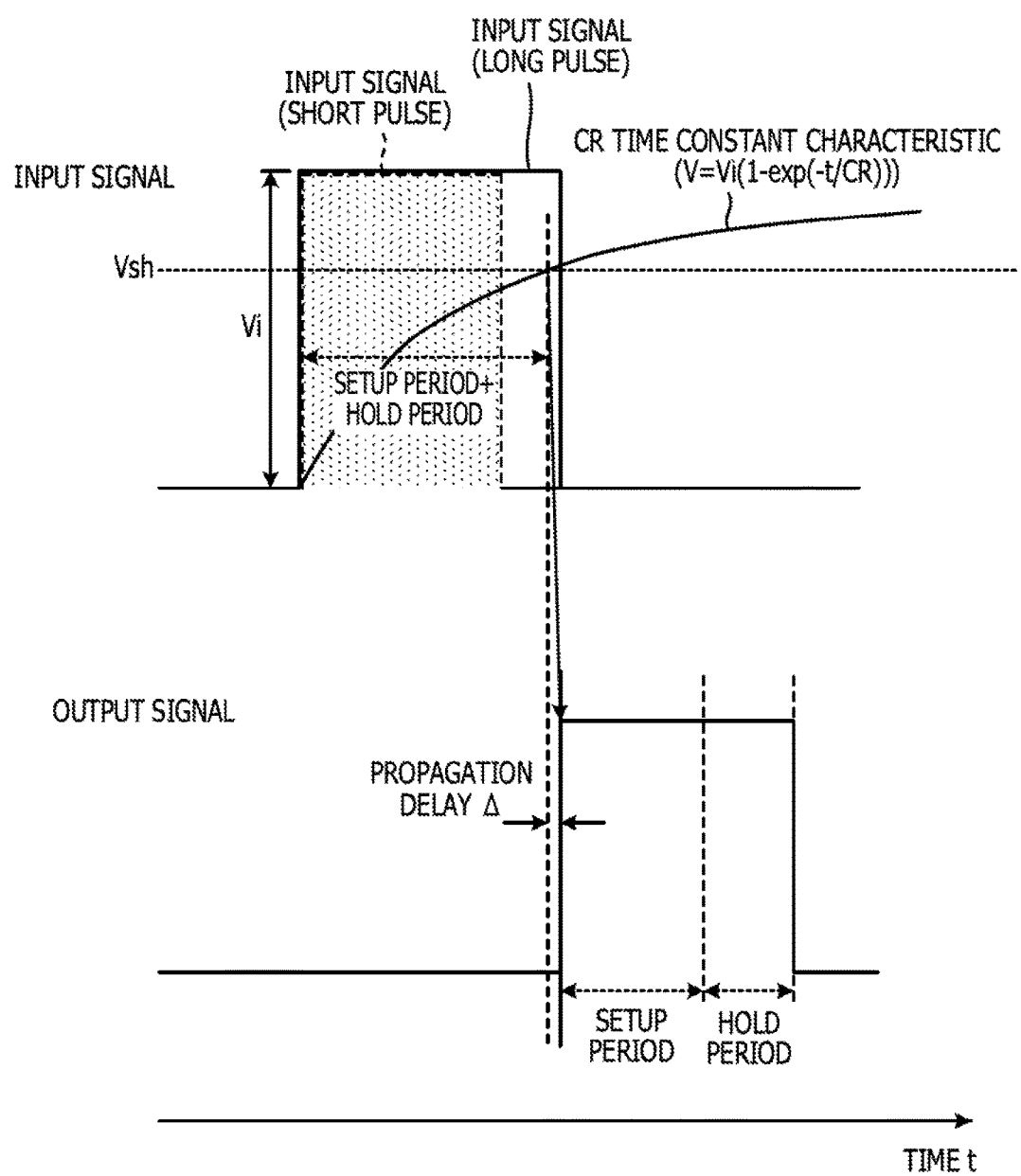
FIG. 11 is an example of the input/output waveform of the short pulse removal circuit.

FIG. 11 is an example of the input/output waveform of the short pulse removal circuit. The pulse selection unit 520 performs removal of a signal of a pulse width corresponding to a period or less, which is obtained by combining the setup period and the hold period by a characteristic of a CR time constant of the integration circuit 521 and a slice level Vsh of the slice level comparison circuit 522.

In FIG. 7, the measurement and adjustment unit 400 measures the pulse width on the high level side and the pulse width on the low level side of the reception data 23 without occurrence of the metastable state, in accordance with the reference clock 30 from the clock correction unit 500 and each of the reference clock pulses. The measurement and adjustment unit 400 generates a threshold value voltage 22 of the comparator circuit 101 in the receiver unit 100 in accordance with the measurement result, and generates the correction data 31 that is to be input to the reception FF 2204 that is at the last stage.

The measurement and adjustment unit 400 includes a clock data extraction unit 410, a pulse count unit 440, a measurement cycle count unit 430, and the difference pulse count unit 450. The clock data extraction unit 410 may be an example of a measurement unit that measures the pulse width of the reception data based on the clock extracted from the reception data. The pulse count unit 440 may be an example of a count unit that measures an elongation and a shortening of the pulse width measured by the measurement unit. The difference pulse count unit 450 may be an example of an adjustment unit that increases a threshold value of the receiver unit when the elongation of the pulse width measured by the measurement unit is larger than a reference value, and reduces the threshold value when the shortening of the pulse width measured by the measurement unit is larger than the reference value.

Figure 12:
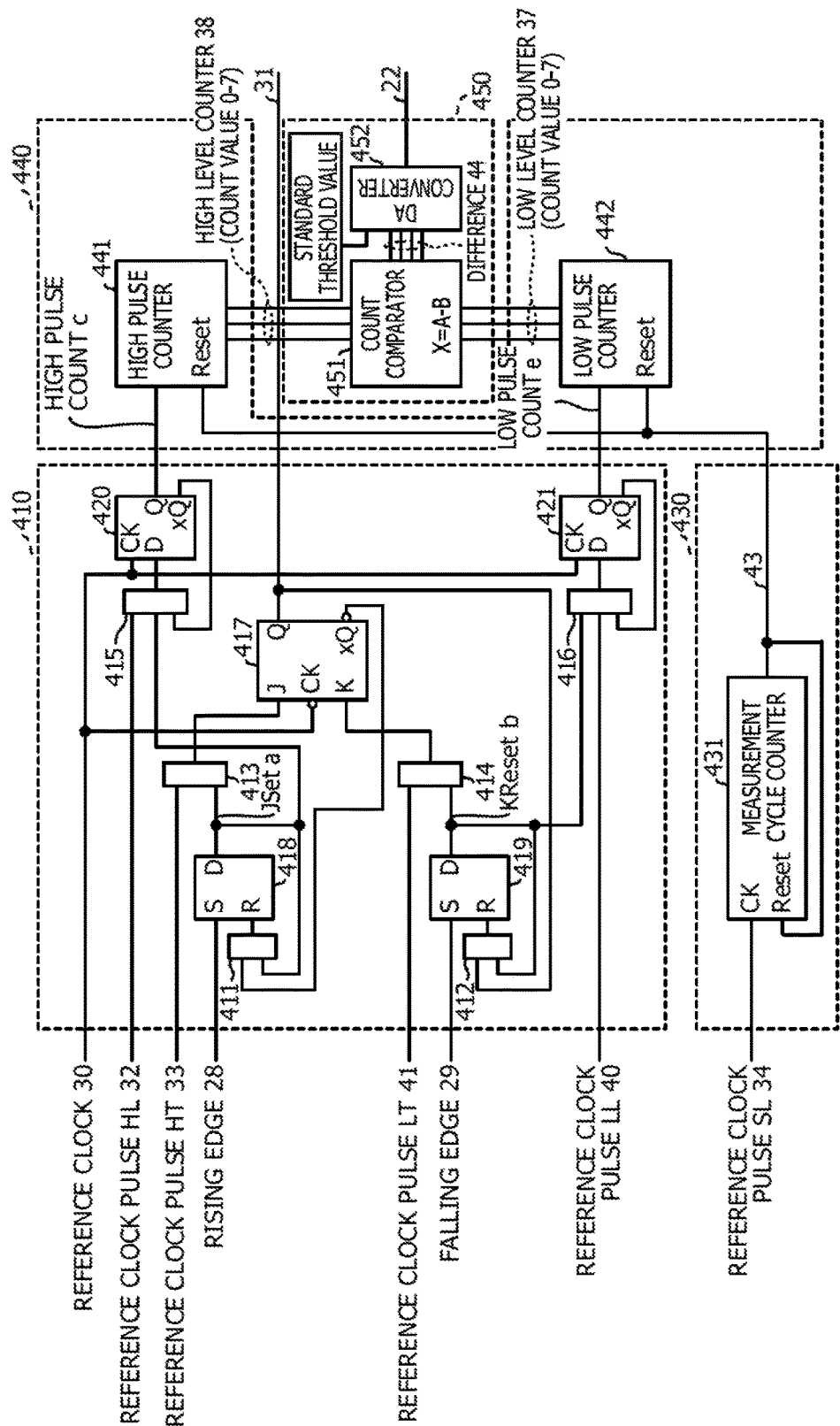
FIG. 12 is an example of a measurement and adjustment unit.

FIG. 12 is an example of the measurement and adjustment unit.

The clock data extraction unit 410 generates the correction data 31, in accordance with the reference clock 30 from the clock correction unit 500 and the reference clock pulses. The clock data extraction unit 410 includes AND circuits 411 to 416, a JK-type FF (JKFF) 417, RS-type FFs (RSFFs) 418 and 419, and D-type FFs (DFFs) 420 and 421.

The clock data extraction unit 410 generates a J input that is to be set to a J terminal of the JKFF 417, based on the rising edge 28 and the reference clock pulse HT 33. The rising edge 28 is detected by the edge detection unit 300. The reference clock pulse HT 33 indicates a signal set so that the pulse on the high level side of the DFF output status 26 is not caused to become the metastable state. The J input is set as an occurrence trigger of the pulse on the high level side of the correction data 31 by the reference clock 30.

The clock data extraction unit 410 generates a K input that is to be set to a K terminal of the JKFF 417, based on the falling edge 29 and the reference clock pulse LT 41. The falling edge 29 is detected by the edge detection unit 300. The reference clock pulse LT 41 indicates a signal set so that the pulse on the low level side of the DFF output status 26 is not caused to become the metastable state. The K input is set as an occurrence trigger of the pulse on the low level side of the correction data 31 by the reference clock 30.

The JKFF 417 outputs the correction data 31 through a Q terminal in accordance with the reference clock 30. A Q output of the JKFF 417 is input to the AND circuit 412. A xQ output of the JKFF 417 is input to the AND circuit 411.

Figure 13:
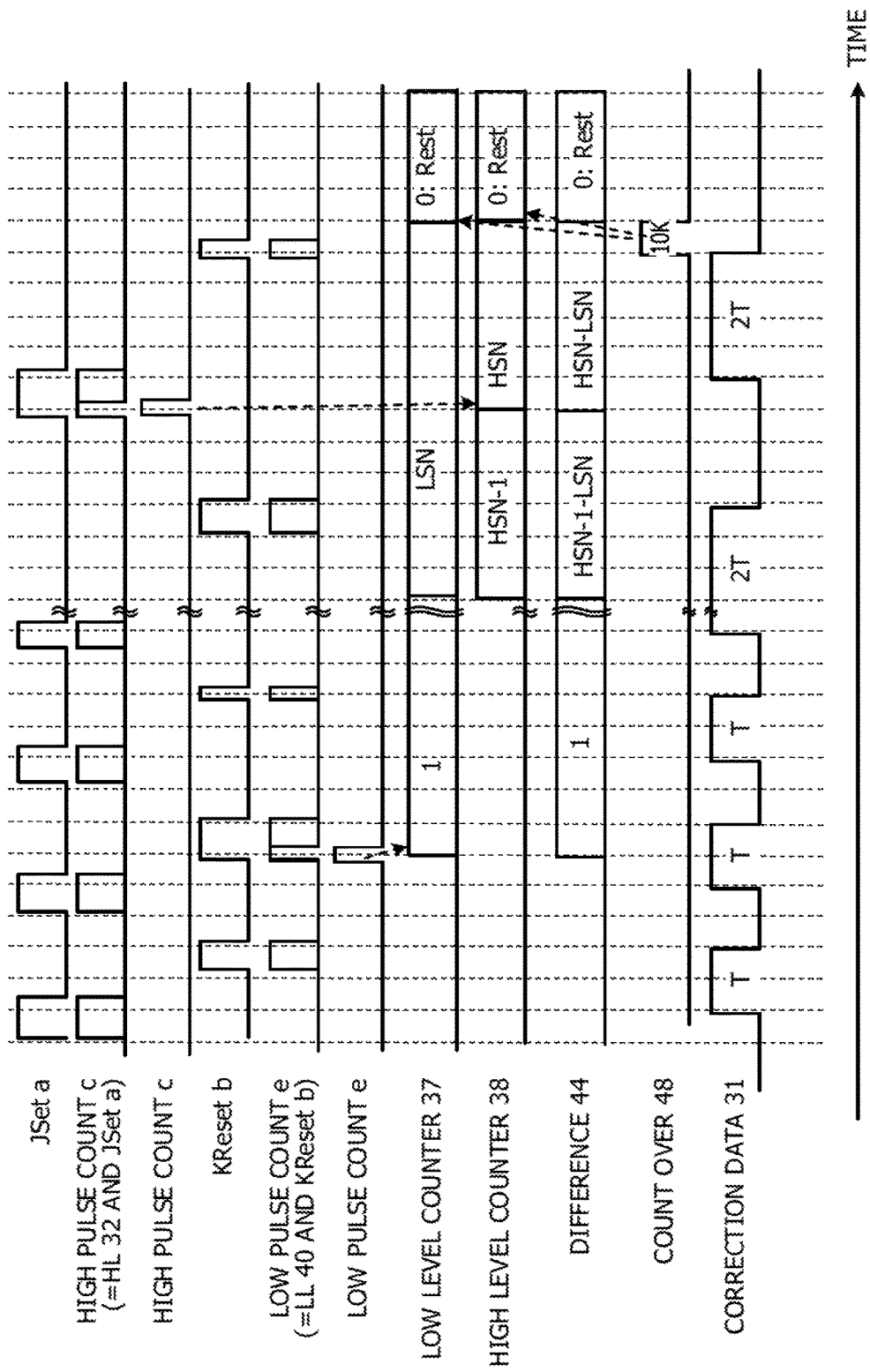
FIG. 13 is an example of processing in the measurement and adjustment unit.

FIG. 13 is an example of processing in the measurement and adjustment unit. When the length from the falling edge of the reference clock pulse HL 32 to the falling edge of a set signal JSet a used to set the pulse on the high level side of the data is the half cycle or more of the reference clock 30, the DFF 420 outputs a high pulse count c (see FIG. 13). The set signal JSet a may be a D output of the RSFF 418. A high pulse counter 441 in the pulse count unit 440 counts the high pulse count c.

In addition, when the length from the falling edge of the reference clock pulse LL 40 to the falling edge of a set signal KRset b used to set the pulse on the low level side of the data is the half cycle or more of the reference clock 30, the DFF 421 outputs a low pulse count e (see FIG. 13). The set signal KRset b is a D output of the RSFF 419. A low pulse counter 442 in the pulse count unit 440 counts the low pulse count e.

A measurement cycle counter 431 in the measurement cycle count unit 430 counts the reference clock pulse SL 34. The measurement cycle counter 431 activates a count over 48 when the counter value of the reference clock pulse SL 34 reaches a certain count over value (for example, 10K). Therefore, the counting in the high pulse counter 441 and the low pulse counter 442 is cleared (reset) (see FIG. 13).

When the elongation of the pulse width on the high level side of the reception data 23 is larger than the certain reference value, a count-up for a high level counter 38 is performed by the high pulse counter 441. When the elongation of the pulse width on the low level side of the reception data 23 is larger than the reference value, a count-up for a low level counter 37 is performed by the low pulse counter 442.

The difference pulse count unit 450 includes a count comparator 451 and a DA converter 452. The count comparator 451 outputs a difference X between a value A of the high level counter 38 and a value B of the low level counter 37.

When the difference X calculated by the count comparator 451 is "0", for example, when there is no difference X, the threshold value voltage 22 of the comparator circuit 101 in the receiver unit 100 corresponds to the center value between the upper limit value and the lower limit value. The maximum count value of the value A on the high level side, for example, "7" corresponds to the upper limit value of the threshold value voltage 22, and the maximum count value of the value B on the low level side, for example, "7" corresponds to the lower limit value of the threshold value voltage 22. The voltage of the DA converter 452 may be set so that the threshold value voltage 22 is changed depending on a difference X as described above.

When the analog output voltage of the DA converter 452 is fed back to the receiver unit 100, the voltage corresponding to the analog output voltage is set as the threshold value voltage 22.

Figure 14:
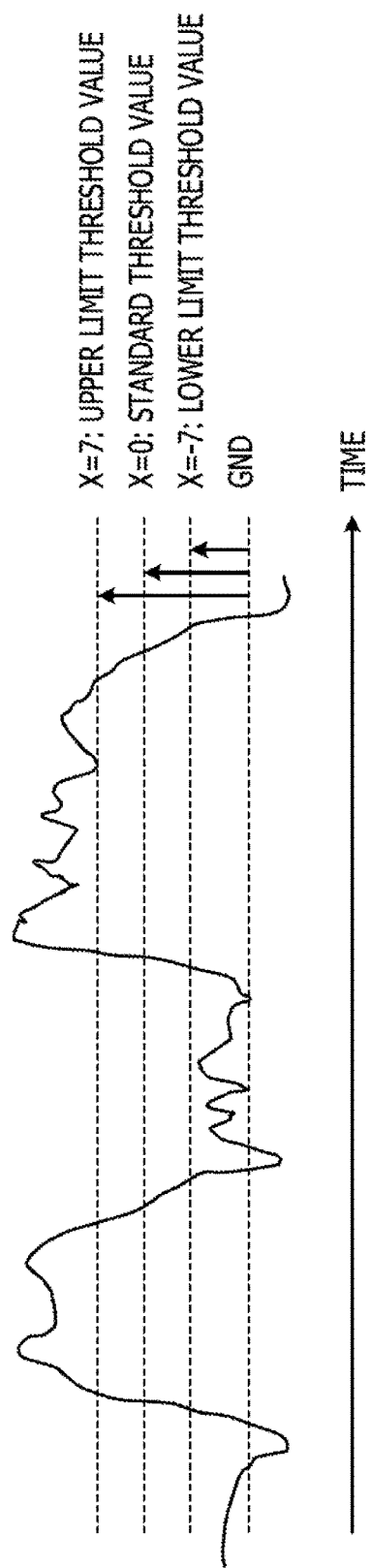
FIG. 14 is an example of a relationship between a single-ended serial input signal and a threshold value.
Figure 15:
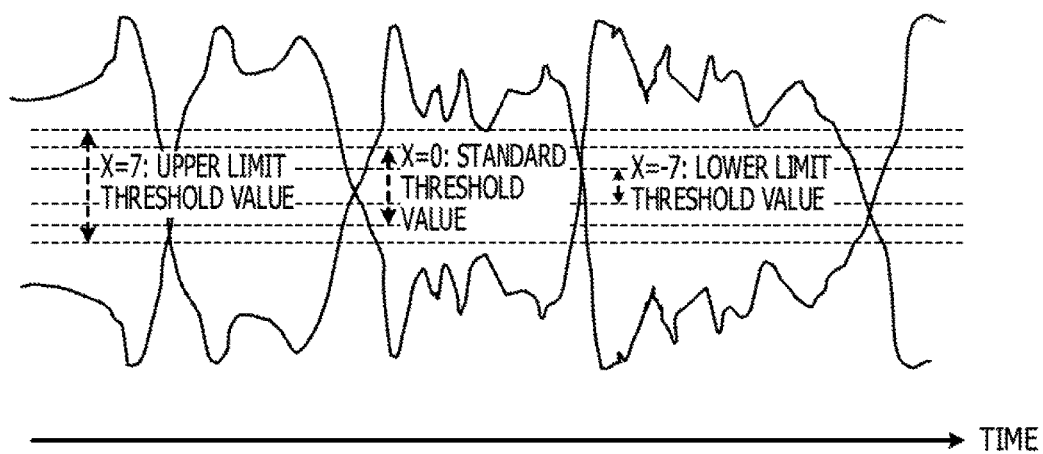
FIG. 15 is an example of a relationship between a differential serial input signal and the threshold value.

For example, the difference X may be obtained as a value of 7 to −7. When the serial input signal 21 input to the receiver unit 100 is a single ended signal, the threshold value voltage 22 is changed depending on a difference X as illustrated in FIG. 14. FIG. 14 is an example of a relationship between a single ended serial input signal and a threshold value. When the serial input signal 21 input to the receiver unit 100 is a differential signal, the threshold value voltage 22 is changed depending on a difference X as illustrated in FIG. 15. FIG. 15 is an example of a relationship between a differential serial input signal and a threshold value. As described above, when a threshold value is set between the upper limit threshold value (X=7) and the lower limit threshold value (X=−7) using the standard threshold value (X=0) of the DA converter 452 as the center value, the jitter that varies in the time axis direction may be absorbed.

For example, the threshold values may be set at the rising and the falling respectively. The pulse width is measured for each of the rising and the falling, and the rising threshold value and the falling threshold value are set to the receiver unit 100. Therefore, adjustment of the pulse width may be performed in each of the rising state and the falling state. The jitter may be reduced to a further degree of accuracy.

Figure 16:
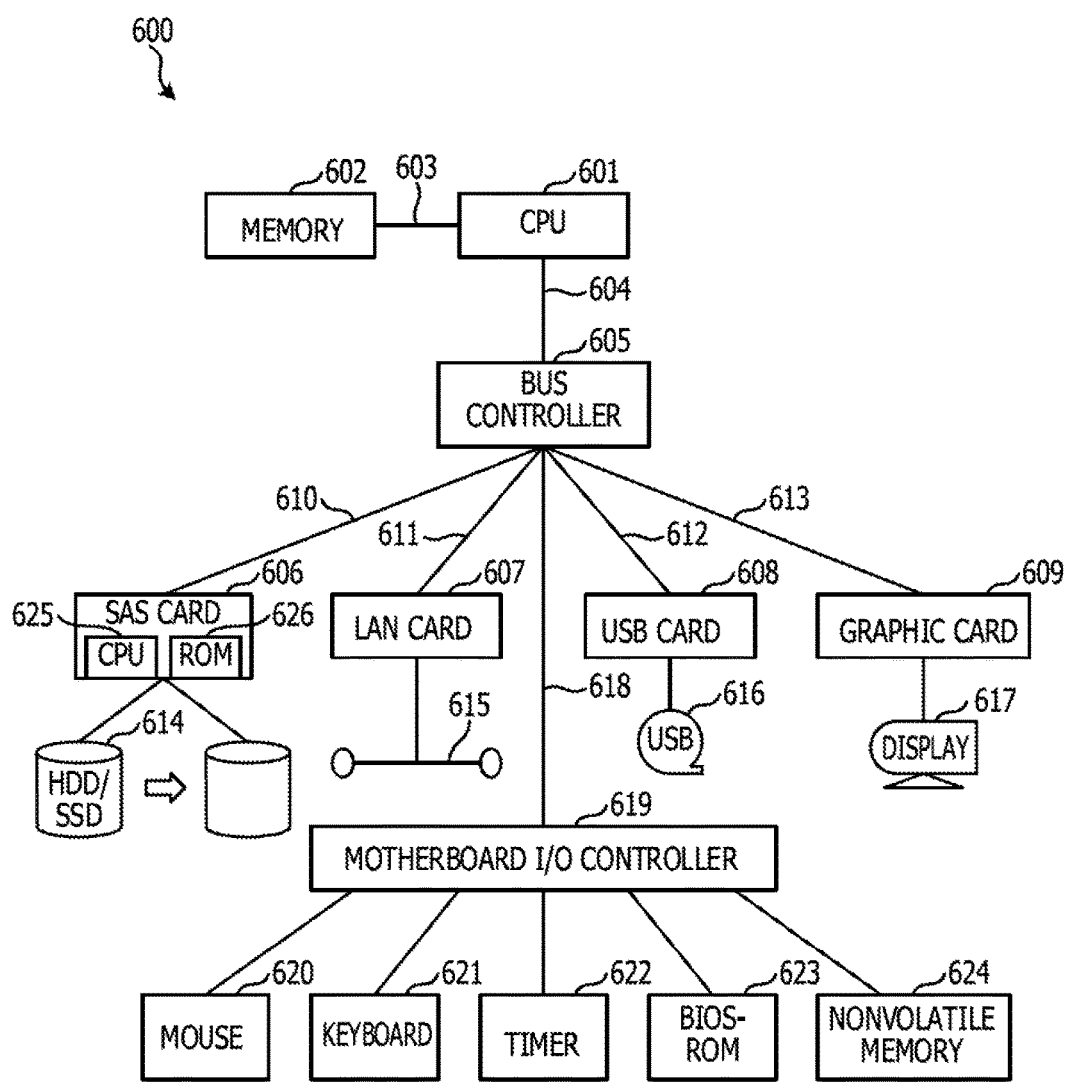
FIG. 16 is an example of a computer.

FIG. 16 is an example of a computer. A personal computer 600 illustrated in FIG. 16 may be an example of an information processing device. The personal computer 600 includes a memory 602, a central processing unit (CPU) 601, a bus controller 605, various cards, and a motherboard input/output (I/O) controller 619.

The memory 602 and the CPU 601 are coupled to each other through a memory bus 603. The CPU 601 and the bus controller 605 are coupled to each other through a host bus 604. The bus controller 605 and the motherboard I/O controller 619 are coupled to each other through a local bus 618. To the motherboard I/O controller 619, a mouse 620, a keyboard 621, a timer 622, a basic input output system-read only memory (BIOS-ROM) 623, and a nonvolatile memory 624 are coupled.

The bus controller 605 is coupled to the various cards through PCIe buses 610 to 613, respectively. The various cards include, for example, a serial attached small computer system interface (SCSI) (SAS) card 606, a local area network (LAN) card 607, a universal serial bus (USB) card 608, and a graphic card 609. A device 614 such as a hard disk drive (HDD) or a solid state drive (SSD) is coupled to the SAS card 606. A LAN cable 615 is coupled to the LAN card 607. A USB 616 is coupled to the USB card 608. A display 617 is coupled to the graphic card 609.

For example, the bus controller 605 may operate as the transmission device 2100 (see FIG. 6), and the SAS card 606 may operate as the reception device 2200 (see FIG. 6). Alternatively, the SAS card 606 may operate as the transmission device 2100, and the bus controller 605 may operate as the reception device 2200. A similar condition is applied to transmission and reception between the bus controller 605 and each of the other cards. The transmission and reception configuration including the transmission device 2100 and the reception device 2200 is not limited to the transmission and reception configuration in which the connection is established through each of the PCIe buses 610 to 613, and may be a transmission and reception configuration in which the connection is established through a connection line of another connection format. For example, a transmission and reception configuration in which the connection is established through the host bus 604 (the CPU 601 and the bus controller 605) may also be applied.

The processing of each of the units (the receiver unit 100, the clock extraction unit 200, the edge detection unit 300, the measurement and adjustment unit 400 and the clock correction unit 500) in the reception device 2200 may be achieved when a program is executed by a computer. For example, when the SAS card 606 operates as the reception device 2200, the program is executed by a CPU 625 in the SAS card 606 and stored in a ROM 626 in the SAS card 606. Even when another device operates as the reception device 2200, a similar condition may be applied.

All examples and conditional language recited herein are intended for pedagogical purposes to aid the reader in understanding the invention and the concepts contributed by the inventor to furthering the art, and are to be construed as being without limitation to such specifically recited examples and conditions, nor does the organization of such examples in the specification relate to a showing of the superiority and inferiority of the invention. Although the embodiments of the present invention have been described in detail, it should be understood that the various changes, substitutions, and alterations could be made hereto without departing from the spirit and scope of the invention.

What is claimed is:

1. An information processing device comprising:
   a receiver that compares a serial input signal to a threshold value and outputs reception data;
   an extraction circuit that extracts a clock superimposed on the reception data from the reception data;
   a measurement circuit that measures a pulse width of the reception data based on the clock;
   a counter that measures an elongation and a shortening of the pulse width; and
   an adjustment circuit that increases the threshold value when the elongation of the pulse width is larger than a reference value, and reduces the threshold value when the shortening of the pulse width is larger than the reference value.

2. The information processing device according to claim 1, wherein
   the pulse width includes a first pulse width on a high level side of the reception data and a second pulse width on a low level side of the reception data.

3. The information processing device according to claim 2, wherein
   the adjustment circuit increases the threshold value when an elongation of the first pulse width is larger than the reference value and reduces the threshold value when an elongation of the second pulse width is larger than the reference value.

4. The information processing device according to claim 1, wherein
   the counter counts a difference between the pulse width of the reception data and a value obtained by multiplying a pulse width of the clock by an integer, and
   the adjustment circuit adjusts the threshold value in such a manner that the difference approaches zero.

5. The information processing device according to claim 2, wherein
   the counter includes
   a first counter that counts an elongation of the first pulse width,
   a second counter that counts an elongation of the second pulse width, and
   a cycle counter that counts a reference clock pulse.

6. An information processing method comprising:
   comparing, by a receiver, a serial input signal to a threshold value and outputting reception data;
   extracting a clock superimposed on the reception data from the reception data;
   measuring a pulse width of the reception data based on the clock;
   measuring an elongation and a shortening of the pulse width; and
   increasing, by a computer, the threshold value when the elongation of the pulse width is larger than a reference value, and reducing the threshold value when the shortening of the pulse width is larger than the reference value.

7. The information processing method according to claim 6, wherein
   the pulse width includes a first pulse width on a high level side of the reception data and a second pulse width on a low level side of the reception data.

8. The information processing method according to claim 7, wherein
   the threshold value is increased when an elongation of the first pulse width is larger than the reference value and the threshold value is reduced when an elongation of the second pulse width is larger than the reference value.

9. The information processing method according to claim 6, wherein
   a difference is counted between the pulse width of the reception data and a value obtained by multiplying a pulse width of the clock by an integer, and
   the threshold value is adjusted in such a manner that the difference approaches zero.

10. The information processing device according to claim 7, further comprising:
    counting an elongation of the first pulse width;
    counting an elongation of the second pulse width; and
    counting a reference clock pulse.

11. A non-transitory computer-readable recording medium storing information processing program that causes a computer to perform processing, the processing comprising:
    comparing a serial input signal to a threshold value and outputting reception data;
    extracting a clock superimposed on the reception data from the reception data;
    measuring a pulse width of the reception data based on the clock;
    measuring an elongation and a shortening of the pulse width; and
    increasing the threshold value when the elongation of the pulse width is larger than a reference value, and reducing the threshold value when the shortening of the pulse width is larger than the reference value.

12. The non-transitory computer-readable recording medium according to claim 11, wherein
    the pulse width includes a first pulse width on a high level side of the reception data and a second pulse width on a low level side of the reception data.

13. The non-transitory computer-readable recording medium according to claim 12, wherein
    the threshold value is increased when an elongation of the first pulse width is larger than the reference value and the threshold value is reduced when an elongation of the second pulse width is larger than the reference value.

14. The non-transitory computer-readable recording medium according to claim 11, wherein
    a difference is counted between the pulse width of the reception data and a value obtained by multiplying a pulse width of the clock by an integer, and
    the threshold value is adjusted in such a manner that the difference approaches zero.

15. The non-transitory computer-readable recording medium according to claim 12, wherein the processing includes:
    counting an elongation of the first pulse width;
    counting an elongation of the second pulse width; and
    counting a reference clock pulse.

* * * * *